United States Patent [19]

Werner

[11] Patent Number: 5,136,040

[45] Date of Patent: Aug. 4, 1992

[54] PREPARATION OF SUBSTITUTED TETRAHYDROPYRIDINES

[75] Inventor: John A. Werner, Indianapolis, Ind.

[73] Assignee: Eli Lilly and Company, Indianapolis, Ind.

[21] Appl. No.: 661,276

[22] Filed: Feb. 26, 1991

[51] Int. Cl.$^5$ .......................................... C07D 211/44
[52] U.S. Cl. ..................................... 546/218; 546/201
[58] Field of Search ................................ 546/201, 218

[56] References Cited

U.S. PATENT DOCUMENTS

| | | | |
|---|---|---|---|
| 3,031,455 | 4/1962 | Holysz | 546/217 |
| 4,072,685 | 2/1978 | Nedelec et al. | 546/249 |
| 4,115,400 | 9/1978 | Zimmerman | 546/192 |
| 4,191,771 | 3/1980 | Zimmerman | 514/317 |
| 4,284,635 | 8/1981 | Zimmerman | 514/317 |
| 4,581,456 | 4/1986 | Barnett | 546/185 |
| 4,891,379 | 1/1990 | Zimmerman | 514/315 |
| 4,992,450 | 2/1991 | Zimmerman | 514/315 |
| 5,037,827 | 8/1991 | Okano | 546/193 |

OTHER PUBLICATIONS

Rahman, *Indian Journal of Chemistry*, 16b, 623-633 (1978).
Larson et al., *Journal of Medicinal Chemistry*, 16, 195-198 (1973).
Diamond, et al., *Journal Medicinal of Chemistry*, 7, 57-60 (1964).
DePuy, et al., in an article entitle "Pyrolytic Cis Eliminations", *Chem. Rev.*, 431-457 (1960).
Barnett, et al., *J. Org. Chem.*, 54, 4795-4800 (1989).
Casy, et al., *Tetrahedron*, 23, 1405-1410 (1967).
O'Conner, et al., *J. Am. Chem. Soc.*, 75, 2118-2123 (1952).

*Primary Examiner*—C. Warren Ivy
*Assistant Examiner*—Celia Chang
*Attorney, Agent, or Firm*—David E. Boone; Leroy Whitaker

[57] ABSTRACT

A process for preparing certain 1,3,4,4-tetrasubstituted-1,2,3,4-tetrahydropyridines is provided as well as certain 4-carbonate-1,3,4-trisubstituted-piperidines.

3 Claims, No Drawings

PREPARATION OF SUBSTITUTED TETRAHYDROPYRIDINES

FIELD OF THE INVENTION

This invention involves process for preparing certain 1,3,4,4-tetrasubstituted-1,2,3,4-tetrahydropyridines.

BACKGROUND OF THE INVENTION 4-arylpiperdines have long been recognized as a valuable class of compounds capable of affecting the central nervous system in animals. Zimmerman, in U.S. Pat. No. 4,191,771 (1980) discloses a process for preparing 1,3,4-trisubstituted-4-arylpiperidines which are described as being analgesics and narcotic antagonists. Zimmerman in U.S. Pat. No. 4,284,635 (1981) discloses 1,2,4,5-tetraalkyl-4-arylpiperidines as being potent analgesics. The procedure disclosed by Zimmerman for preparing these 4-arylpiperidines involves a 1,3,5-trisubstituted-1,4,5,6-tetrahydropyridine intermediate. The preparation procedure disclosed in the U.S. Pat. No. 4,191,771 has the disadvantage of employing diazomethane which is both explosive and toxic.

It would be advantageous to have an improved process for the preparation of the compounds of the Zimmerman patents. It has now been found that the 1,3,4,4-tetrasubstituted-1,2,3,4-tetrahydropyridine intermediate to the compounds of Zimmerman can be conveniently prepared by a process which involves heating a 4-carbonate-1,3,4-substituted-piperidine to eliminate the carbonate moiety followed by a metalloenamine alkylation. The carbonate is preferably resolved prior to the elimination reaction. The elimination reaction provides the 1,3,4-substituted-1,2,3,6-tetrahydropyridine derivative which can be alkylated to provide the desired intermediate.

It has now been found that certain 4-carbonate derivatives provide the desired unsaturated compound in high yields. By contrast elimination of 4-hydroxy-4-arylpiperidines under acidic conditions have been found to primarily provide 1,2,5,6-tetrahydropyridines. Casy et al., Tetrahedron, 23, 1405–1410 (1967) reported that refluxing in aqueous HCl provided a 1.0:2.3 ratio of 5—CH$_3$ to 3—CH$_3$ olefin products. Barnett, et al., J. Org. Chem., 54, 4795–4800 (1989), reported a similar 1.0:2.3 ratio of 5—CH$_3$ olefin to 3—CH$_3$ olefin with toluenesulfonic acid in toluene at reflux; however, 100% H$_3$PO$_4$ at 100° C. provided a 1.0:9.0 ratio of the 5—CH$_3$ olefin to 3—CH$_3$ olefin.

The thermal elimination of esters is well-known as reported by DePuy and King, "Pyrolytic Cis Eliminations", Chem. Rev., 431–457 (1960). Such thermal eliminations in a piperidine ring have been reported by Larson, et al., J. Med. Chem., 1973, Vol. 16, 195–198. Diamond, et al, J. Med. Chem., 1964, Vol. 7, 57–60, disclose eliminations in a nitrogen-containing heterocycle with a basic nitrogen but not a piperidine. The thermal elimination of certain carbonates to produce olefins has also been reported in steroidial molecules, e.g., O'Conner, et al., J. Am. Chem. Soc., 75, 2118–2123 (1953). However the compounds disclosed in this reference do not contain a basic nitrogen. This is in contrast with the instant carbonates which contain a basic nitrogen which have been found in the instant invention to provide the desired olefin in high yields. Rahman has reported the preparation of certain 1,3-dimethyl-4-phenyl-4-piperidyl carbonates. Indian J. Chem., Vol. 16B, 632–633 (1978). However, there is no suggestion of heating the carbonate to provide the corresponding tetrahydropyridine compound.

SUMMARY OF THE INVENTION

This invention involves a method for preparing a compound of the Formula I

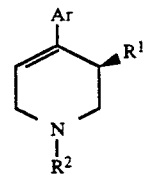

wherein
Ar is aryl;
R$^1$ is C$_1$-C$_5$ alkyl or aryl; and
R$^2$ is C$_1$-C$_{10}$ alkyl, benzyl, CH$_2$R$^3$ in which R$^3$ is C$_2$-C$_7$ alkenyl or C$_3$-C$_6$ cycloalkyl said method comprising heating a compound of a Formula II

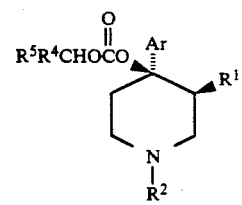

wherein
R$^4$ is hydrogen or C$_1$-C$_{10}$ alkyl and
R$^5$ is C$_1$-C$_{10}$ alkyl or R$^4$ and R$^5$ together are C$_5$-C$_6$ cycloalkyl.

Another embodiment of the instant invention comprises a method for providing a substantially pure stereoisomer of a compound of Formula I which comprises resolving a compound of Formula II by contacting a mixture of stereoisomers of Formula II with (+)-di-p-toluoyl-D-tartaric acid monohydrate, separating the stereoisomers and heating a separated stereoisomer.

A further embodiment of the present invention comprises a compound of Formula II in which R$^4$ is H or C$_1$-C$_{10}$ alkyl, R$^5$ is C$_1$-C$_{10}$ alkyl or R$^4$ and R$^5$ together are C$_5$-C$_6$ cycloalkyl and Ar is 3-(C$_1$-C$_{10}$ alkoxy)phenyl, and R$^1$ and R$^2$ are as defined hereinabove.

DETAILED DESCRIPTION OF THE INVENTION

As used herein the term "C$_1$-C$_{10}$ alkyl" refers a straight chain or branched chain of 1 to 10 carbon atoms including for example ethyl, i-propyl, n-octyl, and the like. The term "C$_1$-C$_5$ alkyl" refers to straight chain or branched chain of 1 to 5 carbon atoms, e.g., methyl, ethyl, n-propyl, i-propyl group and the like.

The term "C$_2$-C$_7$ alkenyl" refers to straight chain or branched olefinically unsaturated groups having 2 to 7 carbon atoms, for example, —CH$_2$CH$_2$CH=CH$_2$, —CH=CH$_2$, —CH$_2$CH=CH$_2$ and the like.

The term "C$_3$-C$_6$ cycloalkyl" refers to alicylic groups having 3 to 6 carbon atoms, for example, cyclopentyl and cyclohexyl. "C$_5$-C$_6$ cycloalkyl" refers to alicyclic groups having 5 to 6 carbon atoms.

The term "aryl" refers to cyclic C$_6$-C$_{10}$ aromatic moieties including phenyl, substituted phenyl, naphthyl, tetralin, indole and the like. Substituted phenyl includes a phenyl group substituted with $C_1-C_5$ alkyl, $O(C_1-C_5$ alkyl), halogen, OH, or disubstituted with independently $C_1-C_5$ alkyl groups, $O(C_1-C_5$ alkyl) or a combination of such groups.

In the instant process the carbonate of Formula II can be conveniently heated to form the olefin of Formula I. The thermal treatment can be accomplished using the compound neat or in an appropriate solvent. It is convenient to use a solvent and remove the alcohol by-product formed by decomposition of the carbonate by distillation. Alternatively the reaction can be carried out in a continuous manner, preferably neat, to allow for ready separation of alcohol by-product. The temperature required for the elimination reaction is dependent upon the carbonate structure. Electron-withdrawing substituents on the carbonate group, e.g., a phenyl carbonate, lowers the temperature required for the thermal elimination.

Useful solvents are materials which dissolve the carbonate compound and are inert at the elimination temperature. Preferably the viscosity of the solvent is low enough to permit easy extraction with aqueous acid to separate the products. More preferably the boiling point is in the range of about 190° C. to about 250° C. although lower boiling materials can be used normally under greater than atmospheric pressure. Examples of preferred solvents include decalin, other hydrocarbons with the desired boiling point range, 2-ethoxyethyl ether, triethylene glycol dimethyl ether, 1,2,4-trichlorobenzene, sulfolane, N-methyl acetamide, and the like. It is normally necessary to heat the carbonate for a period of time ranging from several hours up to 48 hours, with 24 hours being typical when the temperature is in the range of about 190° C.-200° C. A typical reaction is set forth in Scheme I

Scheme I

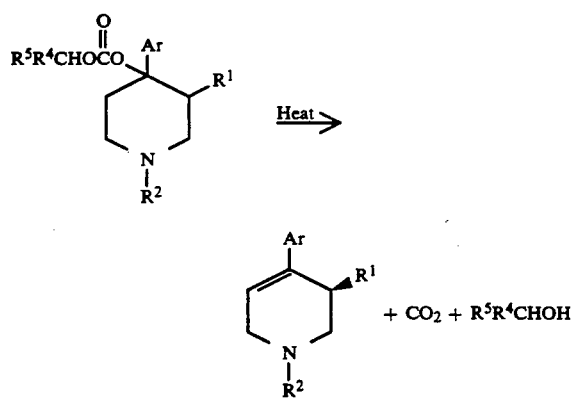

When the carbonate of Formula II is heated neat to accomplish the elimination reaction, temperatures preferably range from about 150° C. to about 250° C. The temperature necessary to provide the elimination reaction depends upon the carbonate which is used. When the carbonate group is a $C_1-C_{10}$ alkyl, the temperature normally ranges from about 170° C. to about 250° C. When the carbamate is phenyl and the 1-nitrogen is protected as a carbamate, the temperature normally ranges from about 150° C. to about 200° C.

The heating time depends upon the particular carbonate derivative as well as the temperature of the elimination reaction. Normally the elimination reaction is followed by an analytical method such as chromatography or proton NMR with the heating continued until the reaction is substantially complete.

The carbonate can be conveniently prepared by contacting a 1,3,4-trisubstituted-4-piperidinol with an appropriate chloroformate as depicted in Scheme 2.

Scheme 2

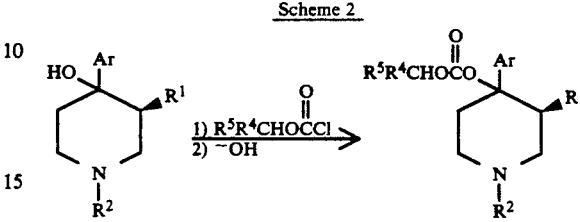

Typically the piperidinol is combined with a solvent such as ethyl acetate or methylene chloride and the chloroformate is added. The reaction mixture is quenched after an appropriate time with a basic material such as sodium hydroxide. The carbonate product can be recovered and purified by standard methods such as preparative chromatography or formation of a salt followed by crystallization.

Alternatively, the desired carbonate can be prepared by first preparing the phenyl carbonate and then contacting it with the desired sodium alkoxide. For example, the i-propyl carbonate (i.e. $R^4$ and $R^5$ of Formula II are each $CH_3$, $R^2$ is $CH_2CH_3$, and $R^1$ is methyl) can be prepared by contacting corresponding phenyl carbonate with isopropyl alcohol and sodium hydride.

The piperidinol can be conveniently prepared by using the appropriately substituted 4-piperidone. A typical preparation is exemplified in Scheme 3 using 1,3-dimethyl-4-piperidone.

Scheme 3

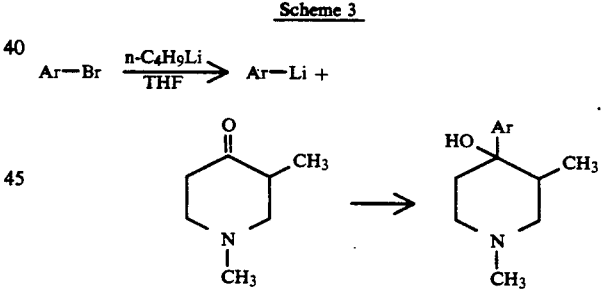

In Scheme 3, the aryl bromide is contacted with butyllithium in the presence of tetrahydrofuran to provide the corresponding lithium derivative followed by the addition of the piperidone.

Although a methyl 1-nitrogen blocking group is depicted in Scheme 3, other 1-nitrogen blocking groups can be used. Typical nitrogen-blocking groups can include other alkyl groups, e.g., $C_1-C_{10}$ alkyl, benzyl, $CH_2-(C_2-C_7$ alkenyl), or $C_3-C_6$ cycloalkyl.

If desired, substantially pure stereoisomers of the particular 1,3,4-trisubstituted-4-arylpiperidine can be provided. These compounds occur as the trans and cis isomers as set forth in column 15 of U.S. Pat. No. 4,018,450 of Zimmerman (1978), incorporated herein by reference in its entirety. The carbonate intermediate of Formula II can be conveniently resolved to provide the substantially pure stereoisomer of Formula II. For example, when $R^1$, $R^2$ and $R^5$ are methyl, $R^4$ is hydrogen, and Ar is 3-isopropoxyphenyl, this can be accomplished by forming the salt of the piperidine carbonate with (+)-di-p-toluoyl-D-tartaric acid, monohydrate. The stereoisomers can be separated by selective crystallization of this salt. Once the stereoisomers have been separated, a base can be added to provide the free carbonate of Formula II.

Alkyl substitution of the compound of Formula I can be accomplished by contacting the compound of Formula I with n-butyl lithium followed by the addition of an alkylating agent such dialkyl sulfate or an alkyl halide. For example, the 4-methyl derivative can be prepared as depicted in Scheme 4. To maximize yield of the enamine reaction product of Formula III, it is desired that the basic character of the 1-nitrogen be maximized. Therefore, $R^2$ should not be an electron withdrawing group such as a carbamate.

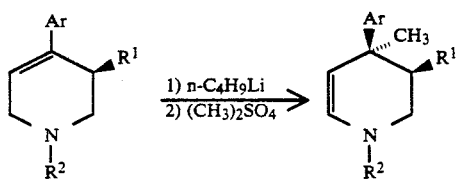

III

The olefin of Formula III can be conveniently reduced using a standard reducing agent such as, for example, sodium borohydride in methanol to provide the corresponding piperidine. This compound can be used in the reaction scheme depicted in columns 3 and 4 of U.S. Pat. No. 4,284,635.

The following examples are intended to illustrate the instant invention and are not to be interpreted as limiting the scope of the invention.

The terms and abbreviations used in the instant examples have their normal meaning unless otherwise designated, for example, "°C." refers to degrees celsius; "N" refers to normal or normality; "mmol" refers to millimole; "g" refers to gram; "ml" means milliliter; "M" refers to molar; "min" refers to minutes; "hr" refers to hours; and "mmHg" refers to millimeters of mercury.

EXAMPLE 1

Preparation of cis(±)-1,3-Dimethyl-4-[3(1-methylethoxy)phenyl]-4-piperidinol.

A. Prepartion of 3-bromo-isopropoxybenzene

The following reagents were combined sequentially: anhydrous ethanol (880 ml), potassium carbonate (448.0 g), 3-bromophenol (386.7 g), 2-bromo-propane (400.0 g) and finally water (88 ml). The mixture was heated at reflux (78° C.) for 16 hours. Water (880 ml) was added to the reaction mixture and 900 ml of solvent was removed by distillation at atmospheric pressure during a 4 hour period. Heptane (880 ml) was added to the reaction mixture and later separated. The aqueous layer was extracted with heptane (80 ml) and the combined organic fractions were washed sequentially with 1N HCl (300 ml), water (300 ml), 1N NaOH (300 ml) and water (300 ml). Removal of the solvent by rotary evaporation (50° C., 5 mmHg) afforded 453.6 g (97%) of crude product. This was distilled through a short path distillation column (81°-85° C., 2 mmHg) to provide 431.5 g of the product as a colorless liquid.

B. Preparation of the Piperidinol

The 3-bromo-i-propoxybenzene (200 g, 0.08703 mol) was combined with THF (tetrahydrofuran) (540 ml) under nitrogen and cooled to about −75° C. n-Butyllithium (565 ml, 0.8306 mol) was added dropwise while maintaining the mixture at less than −70° C. After 2 hours 1,3-dimethyl-4-piperidone (106.7 g, 0.8389 mol) was added while maintaining the temperature of the mixture between −80° C. and −70° C. After stirring for 2 hours at −70° C., the reaction mixture was then added to 6N HCl (280 ml) while maintaining the temperature at 20°-25° C. The pH was adjusted to 1 with 12 N HCl. The aqueous layer was isolated and heptane (320 ml) was added to it along with 50% NaOH (48 ml, to pH of 13-14). The resulting mixture was allowed to stand overnight. The mixture was heated to 45°-50° C. and the upper layer was separated. The remaining aqueous layer was extracted with heptane (320 ml) at 45°-50° C. The combined organic fractions were washed with de-ionized water (120 ml) at 45°-50° C. The resulting organic layer was vacuum distilled at a pot temperature of about 55° C. at 100 mmHg to remove part of the heptane. Crystallization from heptane provided 151.8 g of the named product. Melting point 75.0°-76.0° C.

Analysis: Calc. for ($C_{16}H_{25}NO_2$): C, 72.97; H, 9.57; N, 5.32. Found: C, 72.87; H, 9.56; N, 5.25.

EXAMPLE 2

Preparation of cis-(±)carbonic acid ethyl 1,3-dimethyl-4-[3-(1-methylethoxy)phenyl]-4-piperidinyl ester. (Formula II where $R^1$, $R^2$ and $R^5$ are methyl, $R^4$ is hydrogen and Ar is 3-(1-methylethoxy)phenyl.

4-Hydroxypiperidine (463 g, 1.758 mol) from Example 1 was combined with ethyl acetate (2275 ml) under nitrogen. The solution was cooled to 0°-5° C. and ethyl chloroformate (205 ml, 2.144 mol) was added while maintaining the temperature below 15° C. The reaction mixture was stirred for an additional 3 hours at room temperature. The mixture was then added to 5N NaOH (750 ml) with stirring (to pH of 12-13). The organic layer was separated and washed with de-ionized water. Solvent was removed by evaporation at 50° C. to provide 591 g of the named product is a viscous oil.

Analysis: Calc. for ($C_{19}H_{29}NO_4$): C, 68.03; H, 8.71; N, 4.18. Found: C, 67.82; H, 8.86; N, 4.35.

EXAMPLE 3

Preparation of cis carbonic acid ethyl 1,3-dimethyl-4-[3-(1-methylethoxy)phenyl]-4-piperidinyl ester • (+)-D-2,3-bis[(4-methylbenzoyl)-oxybutanedioic acid (1:1).

The viscous oil product from Example 2 (284.8 g) was dissolved in ethanol (2.6 L) and warmed to 55° C. under nitrogen. (+)-Di-p-toluoyl-D-tartaric acid monohydrate (343.3 g., 0.85 mole) was added and the solution was heated to reflux and then allowed to cool slowly with stirring. After stirring overnight at room temperature, the mixture was cooled to 0°-5° C. before filtering. The filter cake was washed with cold ethanol, air dried for 30 minutes, then vacuum dried at 45°-50° C. Three recrystallizations from ethanol provided 201.7 g of product with a melting point of 153.5°-155° C. (dec). This material had a ratio of isomers of 97:3 by proton NMR on the free base using (+)-2,2,2-trifluoro-1-(9-anthryl)ethanol as a chiral shift reagent.

$[α]_{589}$ = +65.27°.

Analysis: Calc. for ($C_{39}H_{47}NO_{12}$): C, 64.90; H, 6.56; N, 1.94. Found: C, 64.73; H, 6.56; N, 2.04.

EXAMPLE 4

Preparation of cis-(-)-carbonic acid ethyl 1,3-dimethyl-4-[3-(l-methylethoxy)phenyl]-4-piperidinyl ester. (Formula II where $R^1$, $R^2$ and $R^5$ are methyl, $R^4$ is H and Ar is 3-(1-methylethoxy)phenyl).

Sodium hydroxide (18 ml, 18 mmol, 1 M) was added to a suspension of the ditoluoyl tartaric acid salt of the ethyl carbonate (6.58 g, 9.12 mmol), prepared as in Example 3, in hexane (30 ml). After stirring for 10 min, the layers were separated and the organic phase was washed with 15 ml of a solution prepared from equal volumes of water and saturated NaCl followed by 15 ml of saturated NaCl. The solution was dried over $MgSO_4$. Filtration, followed by rotary evaporation afforded 2.99 g (98%) of the ethyl carbonate product.

$[\alpha]_{589} = -6.92°$ (C=1.01 methanol).

Analysis: Calc. for ($C_{19}H_{29}NO_4$): C, 68.03; H, 8.71; N, 4.18. Found: C, 67.89; H, 8.82; N, 4.28.

EXAMPLE 5

Preparation of (−)-1,3-Dimethyl-1,2,3,6-tetrahydro-4-[3-(1-methylethoxy)phenyl]pyridine. (Formula I where $R^1$ and $R^2$ are methyl and Ar is 3-(1-methylethoxy)phenyl).

The product of Example 4 (50.0 g) was combined with decalin (250 ml) and heated at 190°–195° C. for 19 hours under nitrogen while distilling off the ethanol formed. The solution was cooled to 15°–20° C. under nitrogen and 1N HCl (155 ml) was added with stirring. The aqueous fraction was separated and extracted with heptane (2×30 ml). The pH of the aqueous layer was adjusted to about 13 by adding 50% NaOH and the layer was extracted with heptane. 36.5 g of a yellow-orange liquid were removed from the organic layer.

$[\alpha]_{589} = -67.24°$.

Analysis: Calc. for ($C_{16}H_{23}NO$): C, 78.32; H, 9.45; N, 5.71. Found: C, 78.29; H, 9.45; N, 5.66.

EXAMPLE 6

Preparation of cis-1,2,3,4-tetrahydro-1,3,4-trimethyl-4-[3-(l-methylethoxy)phenyl]pyridine. (Formula III where $R^1$ and $R^2$ are methyl and Ar is 3-(1-methylethoxy)phenyl).

The product from Example 5 (19.6 g) was combined with THF (175 ml) and cooled to −15° C. to −20° C. under nitrogen. n-Butyllithium (70.0 ml) was added with stirring over about 0.5 hour while maintaining the internal temperature at about −10° C. to about −20° C. The mixture was stirred for another 0.5 hour at −10° C. to −15° C. and then cooled to −45° to −50° C. Dimethyl sulfate (7.7 ml) was added slowly over 20–30 minutes while maintaining the temperature between −45° C. and −50° C. The mixture was then stirred for an additional 30 minutes at about −50° C. This reaction mixture was then added slowly to a dilute solution of aqueous ammonium hydroxide (15.5 ml aqueous ammonium hydroxide solution plus 55 ml de-ionized water) at 0°–5° C. The mixture was warmed to 20°–25° C. over 30–45 minutes and stirred an additional 2 hours at 20°–25° C. The organic layer was recovered and washed de-ionized water followed by removal of solvent by rotary evaporation to provide 21.44 g of the title compound as an orange liquid.

Analysis: Calc. for ($C_{17}H_{25}NO$): C, 78.72; H, 9.71; N, 5.40. Found: C, 78.50; H, 9.44; N, 5.22.

EXAMPLE 7

Preparation of cis-(+)-1,3,4-trimethyl-4-[3-(1-methylethoxy)phenyl]-piperidine

The product from Example 6 (21.2 g) and methanol (195 ml) were combined under nitrogen and cooled to 0°–5° C. Sodium borohydride (4.2 g) was added slowly while maintaining the temperature below 15° C. The reaction mixture was stirred at room temperature for 3 hours. Acetone (21 ml) was added to the reaction mixture and stirred for 5 minutes. A saturated solution of sodium bicarbonate (25 ml) was added and the mixture stirred for 5 minutes. The organic solvent was removed by evaporation at 50° C. De-ionized water (95 ml) and ethyl acetate (95 ml) were added and the resulting mixture stirred to form a solution. Phases were separated and the organic phase extracted with ethyl acetate (20 ml). The combined organic fractions were washed with de-ionized water (95 ml) and the solvent removed by evaporation at 50° C. to provide the named product as a yellow liquid (20.5 g) (yield, 98.2%).

$[\alpha]_{589} = +63.89°$.

Analysis: Calc. for ($C_{17}H_{27}NO$): C, 78.11; H, 10.41; N, 5.36. Found: C, 78.23; H, 10.34; N, 5.56.

EXAMPLE 8

Preparation of cis-carbonic acid 1,1-dimethylethyl 1,3-dimethyl-4-[3-(l-methylethoxy)phenyl]4-piperidinyl ester. (Formula II where $R^1$ and $R^2$ are methyl, Ar is 3-(1-methylethoxy)phenyl and the $R^5R^4CHOC$-(O)O-moiety is replaced with ($CH_3)_3COC(O)O$—).

Di-t-butyl dicarbonate (9.6 ml, 41.76 mmol, 1.1 equiv) was added via syringe to a solution of the 4-hydroxypiperidine from Example 1 (10.0 g, 37.97 mmol, 1.0 equiv) in THF (50 ml) at room temperature. The reaction mixture was stirred at room temperature for 20 hours. Slow gas evolution was observed. The solvent was removed by rotary evaporation and ether (100 ml) and 1N NaOH (50 ml) were added to the crude product. The layers were separated and the aqueous phase extracted with 25 ml of ether. The combined organic fractions were washed with 3×25 ml of a saturated solution of NaCl and dried over $MgSO_4$. Removal of the solvent by rotary evaporation afforded a tan solid product (13.26 g) (yield, 96%) which was dried overnight at 40° C./5 mmHg.

Analysis: Calc. for ($C_{21}H_{33}NO_4$): C, 69.39; H, 9.15; N, 3.85. Found: C, 69.10; H, 9.29; N, 3.55.

EXAMPLE 9

Preparation of cis-carbonic acid phenyl 1-(phenylcarboxylate)-3-methyl-4-[3-(l-methylethoxy)phenyl]-4piperidinyl ester. (Formula II where $R^1$ is methyl, $R^2$ is $-C(O)OC_6H_5$, Ar is 3-(1-methylethoxy)phenyl, and the $R^5R^4CHOC(O)O$— moiety is replaced by $C_6H_5OC(O)O$—).

Phenyl chloroformate (0.95 ml, 7.55 mmol, 1.2 equiv) was added over 2 min via syringe to a solution of cis-carbonic acid phenyl 1-ethyl-3-methyl-4-[3-(1-methylethoxy)phenyl-4-piperidinyl ester (2.50 g, 6.29 mmol, 1.0 equiv) in toluene (30 ml) at 80°–90° C. The reaction mixture was heated to reflux for 1 hour. Analysis by TLC (1:10 $CH_3OH$/ethyl acetate) shows some residual starting material so an additional 0.25 equiv of phenyl chloroformate (0.2 ml, 1.59 mmol) was added and the solution refluxed for an additional 2 hours. The reaction mixture was cooled to room temperature, diluted with ether (60 ml) and extracted with 1N NaOH (20 ml), 5% HCl (20 ml), saturated NaHCO3 (2×20 ml) and saturated NaCl (2×20 ml). The organic layer was dried over MgSO4. Filtration, followed by rotary evaporation afforded about 4 g of crude product. Purification by flash chromatography (1:5 ethyl acetate/hexane) afforded 2.70 g (87%) of product as a foam.

The i-butyl- and vinyl carbamates were prepared in a similar fashion from the N-ethyl phenyl carbonate in 81% and 97% yield, respectively.

Analysis for vinyl carbamate: Calc. for ($C_{25}H_{29}NO_6$): C, 68.32; H, 6.65; N, 3.19. Found: C, 68.12; H, 6.38; N, 2.96.

EXAMPLE 10

Preparation of cis-carbonic acid 2-propyl 1-ethyl-3-methyl-4-[3-(l-methylethoxy)phenyl-4-piperidinyl ester. (Formula II where $R^1$, $R^4$ and $R^5$ are methyl, $R^2$ is ethyl and Ar is 3-(1-methylethoxy)phenyl].

Isopropanol (50 ml) was added to sodium hydride (0.56 g, 10.9 mmol, 60% dispersion in mineral oil), which has been washed with portions (3×5 ml) of hexane, and the mixture stirred at 25°-30° C. When the hydrogen gas evolution ceased (ca. 15 min), ciscarbonic acid phenyl 1-ethyl-3-methyl-4-[3-(1-methylethoxy)-phenyl]-4-piperidinyl ester (5.02 g, 12.6 mmol) was added in one portion and the solution heated to 60° C. overnight. After 16 h the reaction mixture was cooled, isopropyl alcohol removed and the residue diluted with ethyl acetate (300 ml). The layers were separated and the organic fraction was washed with 1N NaOH (3×50 ml) and a saturated solution of NaCl (3×50 ml) and then dried over MgSO4. Removal of the solvent by rotary evaporation followed by purification of the crude product by flash chromatography (1:10 CH3OH-/ethyl acetate eluent) afforded 4.12 g (82%) of the N-ethyl isopropyl carbonate product.

Analysis: Calc. for ($C_{21}H_{33}NO_4$): C, 69.39, H, 9.15; N, 3.85. Found: C, 69.29; H, 9.07; N, 3.99.

EXAMPLE 11

Preparation of 3,4-dimethyl-4-[3-(1-methylethoxy)-phenyl]-1-(1,2,3,4-tetrahydropyridine)-carboxylic acid phenyl ester. (Formula III where $R^1$ is methyl, $R^2$ is $C_6H_5OC(O)$—, and Ar is 3-(1-methylethoxy)phenyl).

s-Butyllithium (0.27 ml, 0.35 mmol, 1.2 equiv., 1.3 M is cyclohexane) was added dropwise to a THF (10 ml) solution of 3-methyl-4-[3-(1-methylethoxy)phenyl]-1-(1,2,3,6-tetrahydropyridine)-carboxylic acid phenyl ester (102.7 mg, 0.292 mmol) at −70° C. When the addition was complete, the red solution was stirred for 20 min before adding methyl iodide (22 µl, 0.351 mmol, 1.2 equiv.). After 30 min the reaction was quenched by adding 1 ml of a saturated solution of NH4Cl and allowing the solution to warm to room temperature. The reaction mixture was poured into 20 ml of ethyl acetate and 10 ml of water. The layers were separated and the organic fraction washed with saturated NaCl (2×10 ml) and dried over MgSO4. Filtration, rotary evaporation and purification by flash chromatography afforded 30.6 mg (29%) of the named product. This result shows the decrease in yield of desired enamine reaction product relative to that obtained in Example 6 when the basicity of the 1-nitrogen is decreased by substitution with a carbamate compound.

EXAMPLE 12

Resolution of cis-(±) carbonic acid ethyl 1,3-dimethyl-4-[3-(1-methylethoxy)phenyl]-4-piperidinyl ester The indicated acid and the piperidinyl compound were combined in ethanol; the ethanol was stripped off; and recrystallization was attempted from each of the following solvents ethanol, 2-propanol, ethyl acetate, acetone, acetonitrile and toluene. The following results were obtained.

| Acid | Results |
|---|---|
| (+)-3-bromocamphor-8-sulfonic acid | Solid obtained which was soluble in all solvents |
| (+)-10-camphorsulfonic | No crystalline salt |
| L-(−)-dibenzoyltartaric acid | Solid soluble in all solvents |
| (−)-di-p-toluoyl-L-tartaric acid | Good resolution particularly from ethanol |
| (−)-malic acid | No crystalline salt |
| (+)-mandelic acid | No crystalline salt |
| L-(+) tartaric acid | Solid soluble in all solvents |
| 0.5 equivalent dibenzoyltartaric acid | No crystalline salt |
| 0.5 equivalent ditoluoyltartaric acid | No crystalline salt |
| 0.5 equivalent tartaric acid | No crystalline salt |

COMPARATIVE RESULTS

Table I provides results obtained when the indicated carbonate was heated neat at 225° C. for one hour. The following reaction occurred to give the indicated product where Ar is 3-(1-methylethoxy)phenyl.

TABLE I

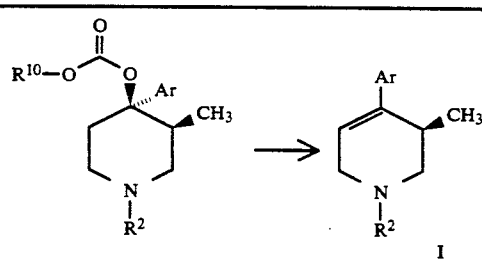

| $R^2$ | $R^{10}$ | % Yield of I | Purity % |
|---|---|---|---|
| a) CH3 | CH3 | mixture of products[1] | |
| b) CH3 | CH3CH2 | 84 | 90[2] |
| c) CH3 | CH(CH3)2 | 77 | 74[2] |
| d) CH3 | CH2CH(CH3)2 | 81 | 87[2] |
| e) CH3 | (C6H5)CH2 | Mixture of products[1] | |
| f) CH3CH2 | CH3CH2 | 77 | 65[2] |
| g) CH3CH2 | CH(CH3)2 | 88 | 91[2] |
| h) CH3CH2 | C6H5 | mixture of products[1] | |
| i) CH3CH2 | C(CH3)3 | mixture of products[1] | |

[1] by proton NMR
[2] HLPC

Table II provides results obtained when the indicated carbonate was heated in decalin at 190° C.-195° C. for 24 hours. The indicated products were obtained according to the following reaction where Ar is 3-(1-methylethoxy)phenyl.

TABLE II

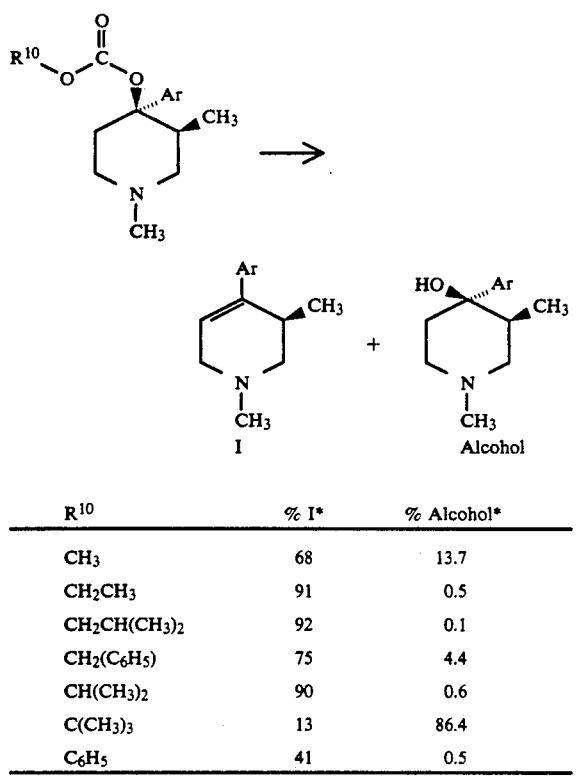

| $R^{10}$ | % I* | % Alcohol* |
|---|---|---|
| $CH_3$ | 68 | 13.7 |
| $CH_2CH_3$ | 91 | 0.5 |
| $CH_2CH(CH_3)_2$ | 92 | 0.1 |
| $CH_2(C_6H_5)$ | 75 | 4.4 |
| $CH(CH_3)_2$ | 90 | 0.6 |
| $C(CH_3)_3$ | 13 | 86.4 |
| $C_6H_5$ | 41 | 0.5 |

*analysis by gas chromatography with internal standard

We claim:

1. A compound of the formula

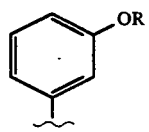

wherein
- $R^1$ is $C_1$–$C_5$ alkyl or an aryl selected from the group consisting of phenyl, substituted phenyl, naphthyl, tetralin or indole wherein said substituted phenyl is a phenyl group substituted with $C_1$–$C_5$ alkyl, $O(C_1$–$C_5$ alkyl), halogen or OH or a phenyl group di-substituted with independently $C_1$–$C_5$ alkyl groups, $O(C_1$–$C_5$ alkyl) or a combination thereof;
- $R^2$ is $C_1$–$C_{10}$ alkyl, benzyl or $CH_2R^3$ where $R^3$ is $C_2$–$C_7$ alkenyl or $C_3$–$C_6$ cycloalkyl;
- $R^4$ is hydrogen or $C_1$–$C_{10}$ alkyl;
- $R^5$ is $C_1$–$C_{10}$ alkyl or $R^4$ and $R^5$ together are $C_5$–$C_6$ cycloalkyl; and
- Ar is

[structure: phenyl with OR substituent]

where R is hydrogen or $C_1$–$C_{10}$ alkyl.

2. The compound of claim 1 wherein $R^4$ is hydrogen or methyl and $R^5$ is methyl, ethyl or isopropyl.

3. The compound of claim 2 wherein $R^1$ is $C_1$–$C_5$ alkyl and $R^2$ is $C_1$–$C_5$ alkyl or benzyl.

* * * * *